United States Patent [19]

Bussey et al.

[11] Patent Number: 4,929,553

[45] Date of Patent: May 29, 1990

[54] PROTEASE FOR SPECIFIC PROCESSING OF SECRETED PROTEINS

[75] Inventors: Howard Bussey, Westmount, Canada; Aleksandra Dmochowska, Warsaw, Poland; David Y. Thomas; Daniel Dignard, both of Montreal, Canada

[73] Assignee: Canadian Patents & Development Ltd., Ottawa, Canada

[21] Appl. No.: 55,555

[22] Filed: May 29, 1987

[51] Int. Cl.[5] ........................ C12N 15/00; C12N 1/00; C12P 21/02

[52] U.S. Cl. ............................... 435/172.3; 435/172.1; 435/255; 435/256; 435/940; 435/942; 435/320; 435/69.1; 530/303; 935/13; 935/28; 935/69; 536/27

[58] Field of Search ................ 435/68, 70, 171, 172.1, 435/272, 224, 320, 172.3, 255, 256; 935/9, 14, 28, 68, 13, 69

[56] References Cited

U.S. PATENT DOCUMENTS 4,546,082 10/1985 Kurjan ............................ 435/172.3

OTHER PUBLICATIONS

Julius et al. (1984), Cell, 37:1075–1089.
Julius et al. (1983), Cell, 32:839–852.
Bussey et al. (1983), Mol Cell Biol, 3:1362–1370.
Kramer et al. (1986), Science, 231:4745.
Kurjan, J. (1985), Mol Cell Biol, 5:787–796.
Fricker et al. (1986), Nature, 323:461–464.
Thim et al. (1986), PNAS, 83:6766–6770.

*Primary Examiner*—Thomas G. Wiseman
*Assistant Examiner*—Anne Brown
*Attorney, Agent, or Firm*—Alan A. Thomson

[57] ABSTRACT

This invention is concerned with the specific processing of secreted proteins in genetically modified yeast cells. The yeast KEX1 gene was cloned and the KEX1 product was shown to be a serine protease, evidently a carboxypeptidase B-like protease. A probable site of processing of polypeptides by the KEX1 gene product is at the C-terminus of the α subunit of the killer toxin, where the mature toxin subunit is followed in the precursor by a pair of basic amino acid residues. Processing likely involves an endoprotease cut following these basic residues, and their subsequent C-terminal trimming by a carboxypeptidase. Consistent with the KEX1 product being this carboxypeptidase is the finding that it is also involved in α-factor pheromone production. In wildtype yeast, KEX1 is not essential for α-factor production, as the final hormone repeat in the prepro α-hormone precursor does not need C-terminal processing to form one copy of the active hormone. However, in a mutant strain where α-factor production requires carboxypeptidase B-like processing, pheromone production is KEX1 dependent. Besides the processing of yeasts' naturally secreted proteins, of which α-factor pheromone and K1 killer toxin are the best characterized examples, the products of KEX1 and KEX2 are required for the processing of some proteins and peptides of commercial importance for example hormones and neuropeptides. High level production of certain commercially important proteins and peptides appears to require the overproduction of the appropriate processing proteases. The cloning of KEX1 on a multicopy plasmid can provide for this overproduction.

8 Claims, 5 Drawing Sheets

PREPRO-α-FACTOR
KEX 2 DIBASIC ENDOPROTEASE
N-TERMINAL PROCESSING
DIPEPTIDYL AMINOPEPTIDASE
STE 13
STE 13
(3x)
C-TERMINAL PROCESSING
CARBOXYPEPTIDASE B-LIKE ACTIVITY
(3x)
KEX1
MATURE α-PHEROMONE
(3x)
MATURE α-PHEROMONE
PREPROKILLER TOXIN
KEX2
SP P2
α γ β
KEX1?
MATURE β-TOXIN
KEX1
MATURE α-TOXIN

```
     AGGATCATTTTGTTAGGTGAGGAATTGCGAGCTTT
-240 TTGGCTATAACTTTCAAGTTTTGTCACCAACATTTATATTTGCTTACTGCAGCCCGGAACCGAAAAACAATGTGGAAAAAGAAAAAAAAGTGGAATATTTTGATAATATAGGAAACATTA
-120 AGAAAAGCGATTTCTTATCATTGTCTTCAACTCCCATCTATTTGAAAAAGCTTGCTGAAGCATACTTTGGTTAAAGAGTACCTTGGCTATAGAATACCGTAGAGATAAAGACCTGAATAG

   1 ATG TTT TAC AAT AGG TGG CTC GGA ACG TGG CTA GCC ATG TCT GCT TTA ATA AGG ATC TCA GTA TCC CTT CCG TCA TCT GAG GAG TAC AAA
   1 Met Phe Tyr Asn Arg Trp Leu Gly Thr Trp Leu Ala Met Ser Ala Leu Ile Arg Ile Ser Val Ser Leu Pro Ser Ser Glu Glu Tyr Lys

  91 GTG GCA TAT GAG CTG TTG CCA GGG TTA TCT GAA GTG CCA GAC CCT TCA AAT ATT CCA CAG ATG CAT GCT GGC CAT ATT CCT TTA CGT TCC
  31 Val Ala Tyr Glu Leu Leu Pro Gly Leu Ser Glu Val Pro Asp Pro Ser Asn Ile Pro Gln Met His Ala Gly His Ile Pro Leu Arg Ser

 181 GAA GAT GCG GAT GAA CAG GAT AGC TCT GAC TTG GAG TAC TTT TTT TGG AAG TTT ACC AAT AAC GAC TCT AAT GGC AAT GTC GAC CGT CCC
  61 Glu Asp Ala Asp Glu Gln Asp Ser Ser Asp Leu Glu Tyr Phe Phe Trp Lys Phe Thr Asn Asn Asp Ser Asn Gly Asn Val Asp Arg Pro

 271 TTA ATT ATA TGG TTA AAT GGT GGA CCC GGT TGC TCT TCC ATG GAT GGT GCC TTG GTC GAA TCC GGC CCT TTT AGG GTG AAT TCA GAC GGT
  91 Leu Ile Ile Trp Leu Asn Gly Gly Pro Gly Cys Ser Ser Met Asp Gly Ala Leu Val Glu Ser Gly Pro Phe Arg Val Asn Ser Asp Gly

 361 AAA CTT TAT CTA AAT GAA GGG TCC TGG ATA TCC AAA GGC GAT CTT TTA TTT ATC GAC CAA CCT ACT GGT ACT GGG TTT TCT GTC GAA CAA
 121 Lys Leu Tyr Leu Asn Glu Gly Ser Trp Ile Ser Lys Gly Asp Leu Leu Phe Ile Asp Gln Pro Thr Gly Thr Gly Phe Ser Val Glu Gln

 451 AAT AAA GAC GAA GGT AAA ATC GAC AAA AAC AAA TTT GAC GAA GAC CTA GAA GAT GTG ACC AAG CAT TTT ATG GAT TTT CTG GAG AAC TAT
 151 Asn Lys Asp Glu Gly Lys Ile Asp Lys Asn Lys Phe Asp Glu Asp Leu Glu Asp Val Thr Lys His Phe Met Asp Phe Leu Glu Asn Tyr

 541 TTC AAG ATT TTT CCA GAA GAC CTC ACT AGG AAA ATC ATA CTA TCG GGT GAA AGT TAC GCT GGC CAA TAC ATA CCA TTC TTT GCC AAT GCA
 181 Phe Lys Ile Phe Pro Glu Asp Leu Thr Arg Lys Ile Ile Leu Ser Gly Glu Ser Tyr Ala Gly Gln Tyr Ile Pro Phe Phe Ala Asn Ala

 631 ATT TTG AAC CAT AAC AAA TTT TCA AAG ATC GAC GGG GAT ACA TAC GAC TTG AAG GCG CTA TTG ATT GGT AAC GGT TGG ATT GAC CCC AAT
 211 Ile Leu Asn His Asn Lys Phe Ser Lys Ile Asp Gly Asp Thr Tyr Asp Leu Lys Ala Leu Leu Ile Gly Asn Gly Trp Ile Asp Pro Asn

 721 ACA CAG TCC CTA TCG TAC CTT CCG TTT GCT ATG GAG AAG AAA CTG ATT GAT GAA AGC AAC CCC AAT TTC AAA CAC TTA ACG AAC GCA CAC
 241 Thr Gln Ser Leu Ser Tyr Leu Pro Phe Ala Met Glu Lys Lys Leu Ile Asp Glu Ser Asn Pro Asn Phe Lys His Leu Thr Asn Ala His

 811 GAG AAT TGC CAG AAT CTG ATA AAC TCT GCC AGT ACA GAT GAG GCA GCC CAT TTT TCG TAT CAG GAA TGT GAG AAT ATT TTA AAC CTT CTA
 271 Glu Asn Cys Gln Asn Leu Ile Asn Ser Ala Ser Thr Asp Glu Ala Ala His Phe Ser Tyr Gln Glu Cys Glu Asn Ile Leu Asn Leu Leu

 901 TTG TCT TAT ACC AGG GAA TCT TCG CAA AAG GGA ACA GCG GAT TGC TTG AAC ATG TAT AAC TTC AAT TTA AAA GAT AGT TAT CCA TCT TGT
 301 Leu Ser Tyr Thr Arg Glu Ser Ser Gln Lys Gly Thr Ala Asp Cys Leu Asn Met Tyr Asn Phe Asn Leu Lys Asp Ser Tyr Pro Ser Cys

 991 GGT ATG AAT TGG CCG AAA GAT ATT TCC TTT GTC AGT AAA TTC TTC AGC ACA CCT GGT GTT ATT GAT TCG TTG CAT CTT GAT TCT GAT AAA
 331 Gly Met Asn Trp Pro Lys Asp Ile Ser Phe Val Ser Lys Phe Phe Ser Thr Pro Gly Val Ile Asp Ser Leu His Leu Asp Ser Asp Lys

1081 ATT GAT CAT TGG AAG GAA TGC ACT AAT AGC GTT GGA ACT AAA TTG TCT AAT CCT ATT TCA AAG CCA TCT ATC CAT TTA TTA CCT GGT CTA
 361 Ile Asp His Trp Lys Glu Cys Thr Asn Ser Val Gly Thr Lys Leu Ser Asn Pro Ile Ser Lys Pro Ser Ile His Leu Leu Pro Gly Leu

1171 CTT GAA AGT GGA ATA GAG ATT GTC TTG TTC AAT GGT GAC AAA GAC TTG ATT TGT AAT AAC AAG GGC GTA TTA GAT ACT ATA GAC AAT CTA
 391 Leu Glu Ser Gly Ile Glu Ile Val Leu Phe Asn Gly Asp Lys Asp Leu Ile Cys Asn Asn Lys Gly Val Leu Asp Thr Ile Asp Asn Leu
```

FIG. 3A

```
1261 AAA TGG GGT GGA ATA AAG GGA TTT AGC GAC GAT GCT GTT TCG TTC GAT TGG ATC CAT AAA TCG AAG AGT ACA GAC GAC AGC GAA GAA TTT
 421 Lys Trp Gly Gly Ile Lys Gly Phe Ser Asp Asp Ala Val Ser Phe Asp Trp Ile His Lys Ser Lys Ser Thr Asp Asp Ser Glu Glu Phe

1351 AGC GGA TAC GTG AAG TAT GAT AGA AAT TTG ACG TTT GTT AGC GTT TAT AAT GCT TCT CAC ATG GTA CCC TTC GAT AAA AGT TTA GTG AGT
 451 Ser Gly Tyr Val Lys Tyr Asp Arg Asn Leu Thr Phe Val Ser Val Tyr Asn Ala Ser His Met Val Pro Phe Asp Lys Ser Leu Val Ser

1441 AGA GGC ATT GTC GAT ATT TAC TCG AAC GAT GTT ATG ATC ATT GAC AAC AAT GGG AAA AAT GTT ATG ATT ACT ACT GAC GAC GAT AGT GAT
 481 Arg Gly Ile Val Asp Ile Tyr Ser Asn Asp Val Met Ile Ile Asp Asn Asn Gly Lys Asn Val Met Ile Thr Thr Asp Asp Asp Ser Asp

1531 CAA GAT GCT ACT ACT GAA AGC GGT GAT AAG CCA AAA GAA AAC CTC GAA GAG GAA GAA CAG GAA GCG CAG AAT GAG GAA GGA AAG GAA AAA
 511 Gln Asp Ala Thr Thr Glu Ser Gly Asp Lys Pro Lys Glu Asn Leu Glu Glu Glu Glu Gln Glu Ala Gln Asn Glu Glu Gly Lys Glu Lys

1621 GAA GGC AAT AAA GAT AAA GAT GGC GAT GAT GAT AAC GAC AAT GAT GAC GAC GAT GAA GAC GAT CAC AAC TCC GAG GGC GAC GAC GAT GAT
 541 Glu Gly Asn Lys Asp Lys Asp Gly Asp Asp Asp Asn Asp Asn Asp Asp Asp Asp Glu Asp Asp His Asn Ser Glu Gly Asp Asp Asp Asp

1711 GAC GAT GAC GAT GAT GAA GAC GAT AAT AAT GAA AAA CAA AGT AAT CAA GGC CTC GAG GAT AGT AGA CAT AAA TCT TCA GAA TAT GAA CAA
 571 Asp Asp Asp Asp Asp Glu Asp Asp Asn Asn Glu Lys Gln Ser Asn Gln Gly Leu Glu Asp Ser Arg His Lys Ser Ser Glu Tyr Glu Gln

1801 GAA GAG GAA GAG GTA GAA GAA TTT GCA GAA GAG ATT TCA ATG TAT AAA CAC AAA GCG GTA GTA GTT ACC ATC GTT ACA TTT TTG ATA GTG
 601 Glu Glu Glu Glu Val Glu Glu Phe Ala Glu Glu Ile Ser Met Tyr Lys His Lys Ala Val Val Val Thr Ile Val Thr Phe Leu Ile Val

1891 GTT TTA GGA GTT TAT GCG TAT GAT AGA AGA GTG AGG AGA AAA GCG CGT CAC ACA ATT TTA GTT GAT CCA AAT AAT AGA CAA CAT GAC AGT
 631 Val Leu Gly Val Tyr Ala Tyr Asp Arg Arg Val Arg Arg Lys Ala Arg His Thr Ile Leu Val Asp Pro Asn Asn Arg Gln His Asp Ser

1981 CCC AAT AAG ACA GTT TCA TGG GCA GAT GAT CTG GAA AGC GGA CTC GGG GCA GAA GAT GAT TTA GAA CAA GAT GAG CAG TTA GAA GGC GGA
 661 Pro Asn Lys Thr Val Ser Trp Ala Asp Asp Leu Glu Ser Gly Leu Gly Ala Glu Asp Asp Leu Glu Gln Asp Glu Gln Leu Glu Gly Gly

2071 GCA CCC ATA AGT AGC ACT TCT AAC AAA GCA GGA TCT AAA TTG AAA ACT AAG AAA AAG AAG AAG TAT ACT AGC CTT CCG AAC ACT GAA ATC
 691 Ala Pro Ile Ser Ser Thr Ser Asn Lys Ala Gly Ser Lys Leu Lys Thr Lys Lys Lys Lys Lys Tyr Thr Ser Leu Pro Asn Thr Glu Ile

2161 GAT GAA TCT TTT GAG ATG ACT GAT TTT TAA CTTGGCAAATAAAAATATATAAAAAATACAGAAAAATAGTTATAATACCTCGCACACGCTTTTCGTAGTAACAGCGACAT
 721 Asp Glu Ser Phe Glu Met Thr Asp Phe —

2271 AAAGATAAATTCTTTAAAGGGTACAATCCATCAAGAACTGACTGTTTTATTTAATTCACACTACTGAACTTCATATTAAAGTGTCGTCATTTAAGTCTAGTAGGTTATATTAATCGCGCA

2391 CAATAGTTTTTTTTTATGCAAACTGTATCACGAATATTTTTTCAGTTTTCGGACCATTTTTTGACATTTTTAACCAGTTTTTAACATTTTTATGGTAGCGTTCTTTTATTTTTCACGTAA

2511 TTGCATTGAAATAGACATAAACGTATAAAATAATATACAAGTAATTAGAGCTTTTGAACGAGATTGTTTAGTGGTTGTTTTAACTCCTTCACAGAAGTTGAAAACTTCAACGCATTCATA
```

FIG. 3B

PROTEASE FOR SPECIFIC PROCESSING OF SECRETED PROTEINS

BACKGROUND AND PRIOR ART

In higher eukaryotes, secreted proteins including peptide hormones and neurotransmitters are synthesized as larger precursors from which they are released in mature form by the action of specific processing proteases (Steiner et al., Ann. N.Y. Acad Sci. 343 1-16, 1980; Douglass et al., Ann Rev. Biochem. 53, 665-715, 1984; Lynch and Snyder, Ann Rev. Biochem. 55 773-799, 1986). Many of these biologically active peptides are flanked within a precursor molecule by pairs of basic amino-acids; endoproteolytic cleavage after these residues is thought to be the initial step in precursor maturation. Further processing often requires removal of the basic amino-acids by a carboxypeptidase B-like enzyme. A metalloprotease showing specificity towards C-terminal arginine or lysine residues was purified from bovine adrenal chromaffin granules (Fricker and Snyder, J. Biol. Chem. 258, 10950-10955, 1983) and recently the gene encoding this protease (named carboxypeptidase E or enkephalin convertase) has been cloned (Fricker et al., Nature 323 461-464, 1986). This enzyme is believed to be involved in a similar processing step, to the KEX1 gene product, in mammalian cells. U.S. Pat. No. 3,625,829 teaches the purification of carboxypeptidase B from pancreas extracts.

The analogous proteolytic maturation of precursor molecules also occurs in the yeast *Saccharomyces cerevisiae.* The α-factor pheromone and K1 killer toxin are the best characterized examples of secreted proteins derived from such processed precursors. Yeast α-factor is a peptide pheromone of 13 amino-acid residues involved in the mating response of haploid cells. It is encoded by two genes: MF α 1 and MF α 2 (Kurjan and Herskowitz, Cell 30, 933-943, 1982; Singh et al., Nucleic Acids Res. 11, 4049-4063, 1983). The α-factor coding sequence occurs repetitively, with either four or two copies within the respective 165 or 120 amino acid precursors encoded by these genes. Biologically active pheromone peptides are separated in the precursors by LysArgGluAla(Glu/Asp)AlaGluAla spacers. The liberation of the pheromone requires the activity of three proteolytic enzymes: an endoprotease recognizing a pair of basic amino-acids, a dipeptidyl aminopeptidase capable of removing N-terminal GluAla repeats and a carboxypeptidase responsible for cleaving C-terminal basic residues (See FIG. 1). The first two enzymes have been identified as the KEX2 and the STE13 gene products, respectively, and both genes have been cloned (Julius et al, Cell 36 309-318, 1983, Cell 37 1075-1089, 1984). A possible candidate for the carboxypeptidase has been suggested on the basis of biochemical evidence (Achstetter and Wolf, EMBO J. 4 173-177, 1985).

The set of processing proteases required for secretion of killer toxin (a small protein secreted by yeast carrying linear M1 double stranded RNA) is less well characterized. The killer toxin protein has been cloned (Thomas et al., U.S. application Ser. No. 06/600,964, filed 16 Apr. 1984). Mature killer toxin consists of two subunits: α and β, which are separated within a precursor by a glycosylated γ region (Bostian et al., Cell 36, 741-751, 1984; Skipper et al., EMBO J. 3 107-111, 1984; and see FIG. 1). Additionally the α subunit is preceded by a 44 amino-acid residue leader, the first 26 residues of which are a signal peptide removed during entry into the endoplasmic reticulum (Lolle and Bussey, Mol. Cell. Biol. 6 4274-4280, 1986). In addition to the signal peptidase, at least three other proteolytic events are necessary to release mature toxin from the precursor: (1) cleavage between the leader remnant and the α subunit (at the P2 site) to generate the authentic N-terminus of the α-subunit, (2) cleavage between the α and γ peptides, (3) cleavage between the γ and β subunits (See FIG. 1). The last cleavage (3) occurs after LysArg residues of the γ peptide and is probably carried out by the KEX2 coded protease. The fact that killer toxin is not secreted from kex2 mutants harboring the M1 dsRNA (Leibowitz and Wickner, Proc. Natl. Acad. Sci. U.S.A. 73 2061-2065, 1976; Bussey et al., Mol. Cell. Biol. 3 1362-1370, 1983) is consistent with this scheme. Enzymes responsible for events (1) and (2) have not been identified.

In the present invention we have focused on the KEX1 gene product. Mutations in this gene lead to failure to process the protoxin (Wickner and Leibowitz, Genetics 82 429-442, 1976; Bussey et al op. cit., 1983) and like kex2 mutations result in a killer minus phenotype. We expected that the KEX1 gene would encode a protease involved in releasing the subunit from the precursor molecule. An endoproteolytic, chymotrypsin-like activity was proposed for this protein based on inhibitor studies (Bussey et al. op. cit., 1983) and a cleavage site in the protoxin was postulated (Bostian et al. op. cit., 1984). To explore this possibility, we decided to clone the KEX1 gene and to characterize the encoded protein. Nucleotide sequence revealed a surprising feature of the gene product, namely extensive homology with carboxypeptidase Y including homology with residues at the active site. We have also found that kex1$^-$null mutations are pleiotropic, affecting not only maturation of the killer toxin, but also of active α-factor mating pheromone. We have found that the KEX1 gene product acts as a carboxypeptidase B-like processing protease in the maturation of these precursors in yeast.

Carboxypeptidase Y (CPY) is a well characterized yeast vacuolar serine protease (Hayasi et al. J. Biol. Chem. 250, 5221-5226, 1975; Martin et-al., Carlsberg Res. Commun. 47, 1-3, 1982; Svendsen et al. Carlsberg. Res. Commun. 47, 15-27, 1982; and see Breddam, Carlsberg Res. Commun. 5, 83-128, 1985, for a review). This yeast protease is only known to be involved as a degradative enzyme and is not involved in protein processing. The cellular location of carboxypeptidase Y and the KEX1 product is different, CPY being found in yeast vacuoles and the KEX1 gene product is thought to be located in the Golgi apparatus. These two protease are also genetically unrelated; CPY cannot complement kex1 mutations.

KEX1 and KEX2 are required for the processing of some proteins and peptides of commercial importance, for example hormones and neuropeptides. Therefore, an application of this present invention is to provide these processing proteases in combination with commercially important proteins and peptides, either together in the same vector or on separate vectors. These processing proteases would provide for the specific processing of the desired secretion polypeptides to yield mature proteins.

SUMMARY OF INVENTION

This invention is concerned with the specific processing of secreted proteins in genetically modified yeast cells.

According to the present invention there is provided a DNA sequence of the type occurring in *Saccharomyces cerevisiae* genomic DNA which encodes a protease and which is capable, when correctly combined with a cloning vector, of expressing a protease upon transformation of a host organism by said vector, said DNA sequence being capable of complementing the kex1 mutation.

In another embodiment of the present ivention there is provided a DNA sequence encoding a protease capable of complementing the kex1 mutation and also incorporating a sequence coding for a desired polypeptide intended to be processed by the expression product of the protease DNA sequence, in which the incorporated sequence is selected from sequences coding for hormones and neuropeptides.

Also according to this invention there is provided recombinant vectors comprising the DNA sequences described above and host organisms transformed by said vectors.

Further according to the present invention there is provided a method for the specific processing of cell-secreted proteins comprising:

(a) providing a recombinant vector comprising the DNA sequence encoding a protease and providing a second recombinant vector comprising the DNA sequence of the cell-secreted protein to be processed;
(b) transforming a host organism with the recombinant vectors of step (a);
(c) culturing the transformed host cells whereby the DNA of the recombinant vectors express both the encoded protease and precursor of the desired polypeptide;
(d) allowing said protease to convert said precursor to said polypeptide; and
(e) recovering said polypeptide.

In another embodiment of the present invention there is provided a method for the specific processing of cell-secreted proteins wherein the recombinant vector comprises the DNA sequence encoding a protease and the DNA sequence encoding the cell-secreted protein to be processed.

In a further embodiment to this invention there is also provided the protease encoded by the DNA sequence capable of complementing the kex1 mutation.

Further according to this invention there is provided a method in vitro processing cell-secreted proteins comprising: (a) incubating the precursor of desired polypeptide with the protease encoded by the DNA sequence capable of complementing the kex1 mutation; (b) allowing said protease to convert said precursor to said polypeptide; and (c) recovering said polypeptide.

There is also provided in this invention, yeast strains of *S. cerevisiae* carrying a null mutation of the KEX1 gene produced by gene disruption of the KEX1 gene.

In another embodiment of the present invention there is provided a method for the specific processing of cell-secreted proteins comprising:

(a) providing a recombinant vector comprising the DNA sequence of the cell-secreted protein to be processed;
(b) transforming the host yeast strains carrying a null mutation of the KEX1 gene with the recombinant vector of step (a);
(c) culturing the transformed host cells whereby the DNA of the recombinant vector expresses the cell-secreted protein, retaining the C-terminal basic residues;
(d) recovering said cell-secreted protein; and
(e) activating said cell-secreted protein by a carboxypeptidase B type protein.

DESCRIPTION OF THE DRAWINGS

In the drawings:

FIG. 3 depicts the nucleotide and derived amino acid sequences of KEX1.

DETAILED DESCRIPTION

Figure 1:
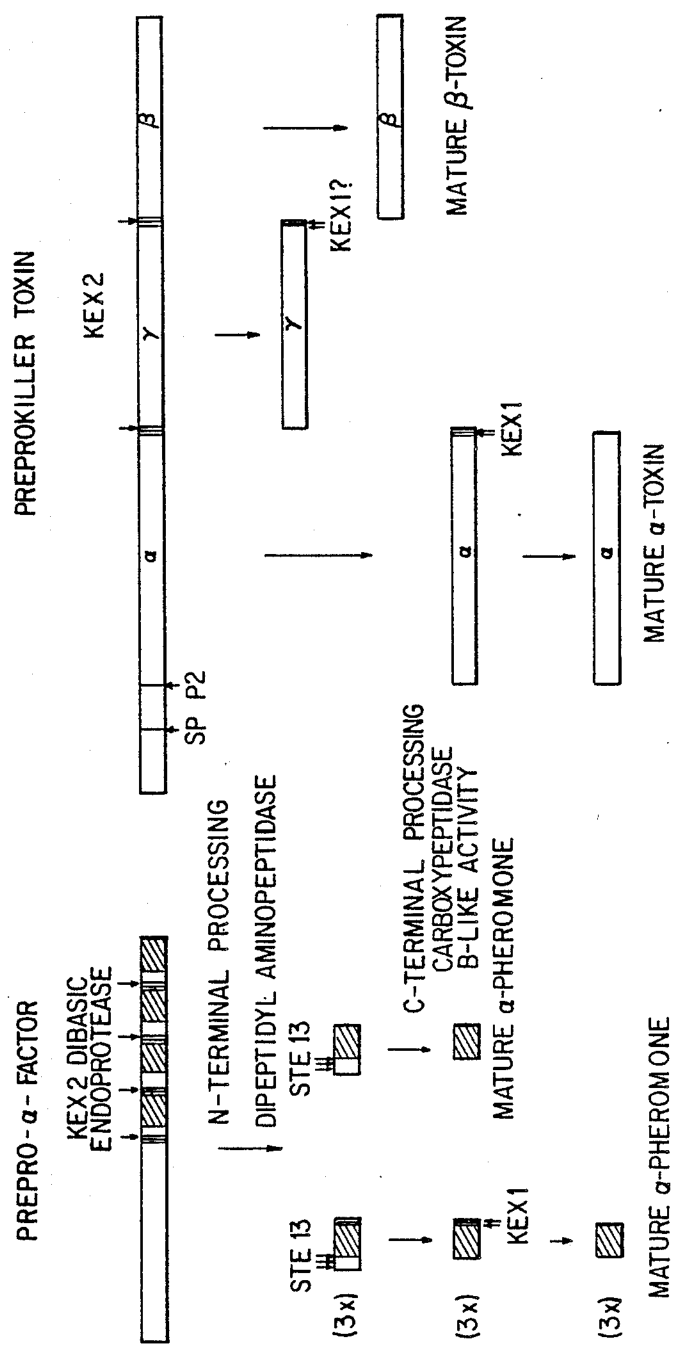
FIG. 1 shows the scheme of proteolytic processing of killer toxin and α-factor precursors in yeast.

This invention is concerned with the isolation of a DNA sequence expressing a protease of protease precursor, the insertion of the DNA sequence into an appropriate vector, the transformation of a host lacking adequate expression of the protease and cultivating of the host to produce the protease. Specifically, this invention is concerned with the isolation and cloning of the KEX1 gene.

In this invention the KEX1 gene was isolated from a *S. cerevisiae* genomic library and selected by its capability of complementing the kex1 mutation in *S. cerevisiae.* Subsequent to its isolation the nucleotide and derived amino acid sequences of KEX1 were determined. With this information now available there are alternate methods which could be used to isolate the KEX1 gene. A nucleotide probe could be used to select for the messenger RNA (mRNA) for the gene of interest. From this mRNA a double stranded cDNA can be produced, using known techniques, which would encode the protease protein. Probes will generally be of at least 25 nucleotides, more usually at least about 30 nucleotides but may be 200 or more nucleotides. Alternatively, a nucleotide probe could be used to isolate the KEX1 gene from yeast genomic DNA. Another possible method of obtaining the KEX1 gene or protease would be to chemically synthesize the gene or protein, however this method would not be preferred due to the size of the gene and protein. The DNA sequence could also be a combination of synthetic and natural sequences.

The DNA nucleotide sequence of the KEX1 gene is shown in FIG. 3. It would be obvious to those skilled in the art that certain single or multiple base substitutions, deletions, insertions or inversions could be possible without changing the function of the resulting protein.

The choice of vector and manner of insertion of the gene into the vector may vary widely. Various vectors include plasmids, phage, viruses, minichromosomes, or the like. The choice of vector will depend on the host. In the Examples in this invention the vector used (YCp50) is a shuttle vector containing *E. coli* and yeast DNA sequences. However, any vector could be used provided it contains suitable selectable markers for the appropriate host and a cloning site for the insertion of yeast genomic DNA. In the Examples in this invention the host organism was *S. cerevisiae.* Therefore, there was no requirement that the vector contain yeast gene control regions such as: a yeast promotor, an upstream sequence for the entry of RNA polymerase, a mRNA initiation site for transcription, a translation initiation site or a translation termination site. All of these control regions are provided with the cloned KEX1 gene sequence. However, if other host organisms besides species from the genus Saccharomyces, such as *Schizosaccharomyces pombe,* mammalian cell lines, insect cell lines, filamentous fungi, or other cell types where KEX1 activity is lacking, were used, the appropriate control regions would need to be provided by the cloning vector.

Molecular cloning has become a powerful tool for the amplification of specific DNA fragments and their subsequent isolation in high yields. Two steps are involved in molecular cloning. First the DNA fragments are joined in vitro to an autonomously replicating cloning vehicle molecule, plasmid DNA or phage NDA. These recombinant cloning vehicles are then introduced into a host cell by transformation. Yeast is finding application for the production of proteins and peptides of commercial importance; some of these (for example hormones and neuropeptides) require processing by both the KEX2 and KEX1 gene products. Some of these proteins include: prepro insulin and prepro opiomelanocortin. High level production of such peptides may also require the overproduction of appropriate processing proteases, indeed there is evidence that STE13 product can be limiting in the processing of α-factor (Julius et al. Cell 32, 839–852, 1983), and some evidence that C-terminal trimming of insulin chains is not completed in yeast (Thim, et al. Proc. Natl. Acad. Sci. U.S.A. 83, 6766–6770, 1986). The identification and cloning of these protease coding genes makes feasible the possible construction of such hyperprocessing yeast strains.

The gene encoding the selected proteins to be processed can be inserted in the same cloning vector as the genes encoding the processing proteases. This novel cloning vector can then be used to transform the appropriate host organism. Upon culturing the transformed host organism the selected secreted mature protein will be produced. Alternatively, the gene encoding the selected secreted protein to be processed can be present on a cloning vector separate from one carrying the genes encoding the processing proteases. These two distinct cloning vectors can be used to co-transform the appropriate host organism. As in the other method, upon culturing the transformed host organism the selected secreted mature protein will be produced. Both of the methods described above are directed to a method of in vivo processing. The processing protease can also be used in vitro to process the selected secreted proteins. In this method the unprocessed secreted proteins would be processed in vitro by the purified processing enzymes.

An additional intended use is to take advantage of the fact that one can engineer the complete absence of the KEX1 protease from yeast cells by gene disruption (Rothstein, Methods Enzymol. 101 202–211, 1983). In this invention the KEX1 gene was disrupted by the insertion the LEU2 gene into the SalI site within the KEX1 gene. It is of course obvious that other DNA markers could be inserted into the SalI site or other restriction sites within the KEX1 coding region; for example the BamHI, XhoI or NcoI restriction sites. In addition gene disruption was accomplished in this invention by replacing a fragment of the KEX1 coding sequence with a DNA fragment carrying a LEU2 or URA3 marker. As with the gene insertion method other DNA markers could be used to replace a fragment of the KEX1 coding sequence. The resulting yeast strains would carry a null mutation of the KEX1 gene. This allows for the production of precursors retaining the C-terminal basic residues, which will often not have biological function. Such precursors can then be activated at will (either by the KEX1 protease or by carboxypeptidase B) at some later stage when needed. An example here would be to arrange the slow activation of insulin and its orderly release into the serum of a diabetes patient, an improvement on the boom-bust cycle provided by conventional injection.

EXAMPLE 1: Isolation of te KEX1 Gene

Figure 2:
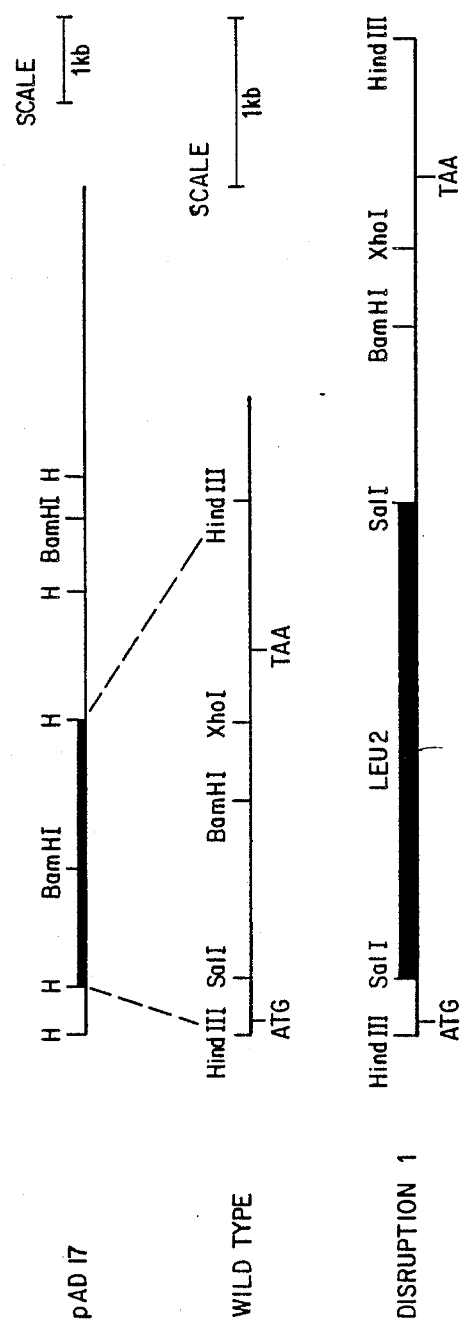
FIG. 2 shows the structure (restriction map) of chromosomal DNA in the KEX1 region from wild type and kex1− disrupted strain.

A kex1 mutant, carrying M1 dsRNA, but phenotypically killer-minus (K−) (strain DGY16a, genotype of all strains found in Table 1), was transformed with a yeast genomic library based on vector YCp50 (Kuo and Campbell, Mol. Cell. Biol. 3 1730–1737, 1983). Transformants were screened for the secretion of active killer toxin, as described by Lolle et al. (EMBO J. 3 1383–1387, 1984). Three positive colonies were found among 35000 tested. All three killer-plus (K+) transformants carried an identical plasmid with a 10.3 kb insert, capable of complementing the kex1 mutation. The restruction map of the insert in plasmid, pAD17, is presented in FIG. 2. Southern blot analysis (Southern J. Mol. Biol. 98, 503–517, 1975) confirmed the presence of the cloned fragment in yeast genomic DNA (results not shown). Deletion analysis and subcloning indicated that a 3.1 kb HindIII fragment was sufficient to complement the kex1 mutation (see FIG. 2.). This fragment encoded a 2.3 kb mRNA transcript, as detected by Northern blot hybridization (Thomas, Proc. Natl. Acad. Sci. U.S.A. 77 5201–5205).

TABLE 1

Yeast strains

| Strain | Genotype | Source |
|---|---|---|
| DGY16a | MAT α his3-A200 ura3-52 ade2-10 kex1-1 [KIL-kl] | |
| DGY7a | MAT α his ura1 leu2-3, 2-112 trp1 [KIL-kl] | |
| DGY7a-4 | MAT α his ura1 leu2-3, 2-112 trp1 kex1::LEU2 [KIL-kl] | |
| Sc25k | MAT α ade1 leu2-3, 2-112, ura3-52 [KIL-kl] | |
| Sc25d | MATa/MAT α ade1/ade1 leu2-3, 2-112/ leu2-3, 2-112 ura3-52/ura3-52 [KIL-kl] | diploidised Sc25k |
| Sc25k-13 | MAT α ade1 leu2-3, 2-112 ura3-52 | |

TABLE 1-continued

| Strain | Genotype | Source |
|---|---|---|
| | Yeast strains | |
| | kex1::LEU2 [KIL-kl] | |
| 5026 | MATa met13 leu2 trp5 cyh2 aro2 lys5 ade5 | |
| Sc25k-13-15 | MATa lys5 aro2 met13 ura3 kex1::LEU2 [KIL-kl] | spore from cross of 5026 × Sc25k-13 |
| 421 | MATa lys2 arg1 kex1-4 | Reed Wickner |
| 411 | MATa arg1 thr1 kex1-6 | R. Wickner |
| 519 | MATa leu2 lys1 kex1-8 | R. Wickner |
| 1315 | MATa/MAT α ura3/ura3 kex1::LEU2/ kex1::LEU2 ade1/ADE1 leu2-3, 2-112/LEU2 aro2/ARO2 met13/MET13 [KIL-kl] | diploid of Sc25k-13-15 × Sc25K-13 |
| 11D | MAT α ura3 leu2 his3 [KIL-ko] | |
| 4A | MATa ura3 trp1 leu2 [KIL-ko] | |
| ADY411 | MATa/MAT α ura3/ura3 leu2/leu2 trp1/TRP1 his3/HIS3 [KIL-ko ] | diploid of 11A × 4D |
| ADY411-9-5 | MAT α ura3 leu2 his3 kex1::URA3 [KIL-ko] | spore from ADY411 following kex1 disruption |
| S6 | wt | D. Rogers (Lolle et al. 1984) |
| XMBL-12b | MATa ilv 9 arg9 ura1 sst1 [KIL-kl] | M. Whiteway |
| M171-1c | MATa ura3 his3 leu2 sst2 | M. Whiteway |

To prove that the cloned DNA contained the KET1 locus, two types of experiment were performed. First, the pAD17 insert was hybridized to a nitrocellulose blot of yeast chromosomes separated by agarose-gel pulse-field electrophoresis (Carle and Olson, Proc. Natl. Acad. Sci. U.S.A. 82, 3756–3760, 1985). A strong positive signal was obtained for chromosome VII. This result is consistent with genetic mapping of the kex1 locus to the left arm of chromosome VII (Wickner and Leibowitz, op. cit. 1976). Weaker hybridization to other chromosomes was also observed, due to the presence of repetitive elements within the insert. Secondly, the original location of the cloned fragment within the yeast genome was determined by genetic analysis. The complementing DNA fragment was disrupted by insertion of the LEU2 marker, which was obtained by introducing 2.8 kb SalI fragment with the LEU2 gene (derived from plasmid pYF91) into the SalI site within the KEX1 gene (see FIG. 2—Disruption 1). This fragment was introduced into the genome of the wild type strain (DGY7a) using the one-step gene replacement method (Rothstein, op cit., 1983), through the use of a HindIII fragment for transformation of the recipient yeast strains. In this disclosure disruptions of KEX1 have been designated as kex1$^-$. The resulting killer-minus (K$^-$) mutant (DGY7a-4) was crossed with a series of kex1 mutant strains (421, 411, 519, see Table 1) to examine its complementation group. In all cases the diploids had a K$^-$ phenotype. Analysis of 17 tetrad derived from the cross with strain 421 showed a 4:0 segregation for the kex$^-$: kex$^+$ phenotype, demonstrating close linkage of the disrupted locus and kex1 allele. These results taken together indicate that integration of the cloned fragment into the yeast genome occurred at the KEX1 locus and that we have cloned the KEX1 gene.

The cloned KEX1 gene was disrupted by replacing a 1.5 kb fragment of the coding sequence with a DNA fragment carrying a LEU2 or URA3 marker. These constructs were used to demonstrate that the KEX1 gene does not have an essential vital function in yeast growth under the conditions tested. Furthermore, it was also shown that the disruption did not affect sporulation efficiency or spore viability was ascertained by sporulating a diploid which was homozygous for the disrupted KEX1 locus.

The nucleotide sequence of the KEX1 gene, for both DNA strands, was determined using the dideoxy method described by Sanger et al. (Proc. Natl. Acad. Sci. U.S.A. 74, 5463–5467, 1977). Subclones of suitable restriction fragments were made in M13mp8 and M13mp9 vectors (Yannisch-Perron et al. Gene 33 109–119, 1985) DNA primers were either the universal M13 sequencing primer or primers synthesized to be complementary to parts of the KEX1 DNA sequence. DNA sequence analysis revealed one long open reading frame uninterrupted by any splicing consensus sequences (Langford and Gallwitz, Cell 33 519–527, 1983) (See FIG. 3). Three AUG codons are present in the same reading frame at the beginning of the putative coding region. In order to identify the initiation codons, the 5′ end of the KEX1 mRNA was mapped using two synthetic primers PEI 5′-TGAGATCCTTATTAAAG-CAGA-3′ and PE2 5′-TAAAGGAATATGGCCAG-CATG-3′ complementary to nucleotides 40-61 (PEI) and 154-174 (PE2) of the extended ORF. The oligonucleotides (2 pmoles) were labelled at their 5′ end using T4 polynucleotide kinase and an excess $^{32}$P-ATP. The labelled primer (2 pmoles) was annealed with total yeast polyA+ RNA (10 μg) at 50° C. in PIPES buffer (0.4M NaCl, 100 mM PIPES, pH 6.4). Primer extension was with AMV reverse transcriptase (10 units) in 50 mM Tris-HCl, pH 8.2, 10 mM DTT, phenol extracted and run on a sequencing gel alongside a dideoxynucleotide sequencing run of the KEX1 gene primed with the same primer.

Transcription appeared to initiate at several sites, all upstream of the first AUG (FIG. 3). Five major transcription initiation sites were found at position −67, −68, −69, −78, −79 and 5 minor ones at positions −38, −51, −52, −95, −114 (FIG. 3). Such heterogeneity at the 5′ end of mRNAs is known for some genes in yeast (McIntosh and Haynes, Mol. Cell. Biol. 6 1711–1721, 1986). Upstream of the transcription initiation sites are three candidates for a TATA box (See FIG. 3). The sequence TAG . . . TAGT . . . TTT, postulated as a transcription termination signal in yeast (Zaret and Sherman, Cell 28 563–573, 1982) is found downstream of the coding sequence (nucleotides 2227–2285). A putative polyadenylation site AATAAA (Fitzgerald and Shenk, Cell 24, 251–260, 1981) is also present at position 2198.

Figure 4:
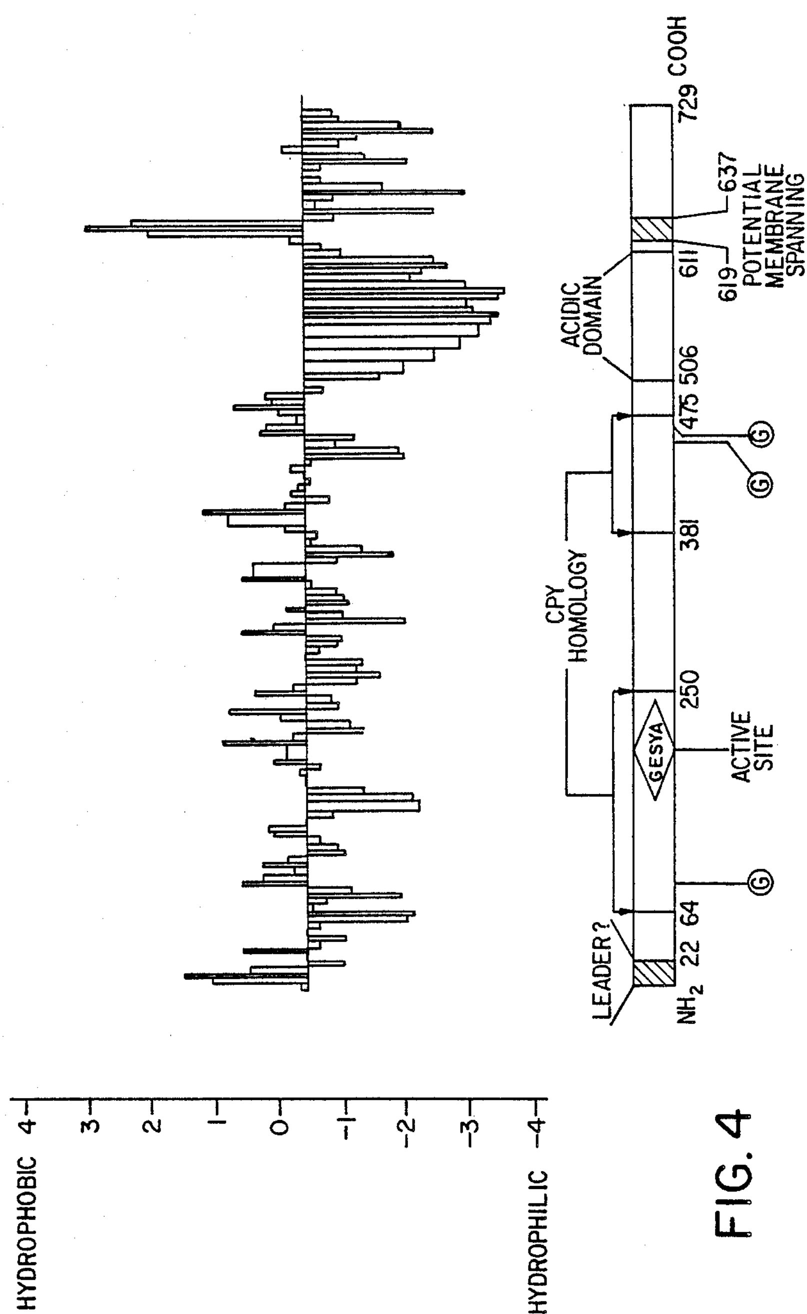
FIG. 4 shows the structure of the KEX1 encoded protein. The diagram at the top represents the hydropathy profile of the KEX1 product and the box structure below depicts the main structural features of the protein as discussed in the text.

The KEX1 gene encodes a protein consisting of 729 amino-acid residues, of calculated molecular weight 82,238. The hydropathy profile determined according to Kyte and Doolittle (J. Mol Biol. 157 105–132, 1982) demonstrates the presence of two hydrophobic regions (FIG. 4). The first, situated at the N-terminus, is a reasonable candidate for a signal sequence (Watson, Nucl. Acids Res. 12, 5145–5156, 1984) capable of directing the KEX gene product into the endoplasmic reticulum.

Furthermore, the sequence surrounding the Ser 22 fulfills the rules (von Heijne, J. Mol. Biol. 172 243–251, 1984) for a signal cleavage site. The second hydrophobic region, situated 100 residues from the C-terminus of the KEX1 protein contains 18 amino-acid residues and possibly functions as a membrane spanning domain of the kind seen in many transmembrane proteins for anchoring of the protein to the membrane location (Kyte and Doolittle, op. cit. 1982). Four potential glycosylation sites (AsnXSer/Thr) are found throughout the amino-acid sequence. Three are situated on the N-terminal side of the putative membrane spanning domain. Interestingly, also N-terminal to this hydrophobic region, is a tract of 105 residues very rich in aspartic and glutamic acids. In some places these negatively charged aminoacids form stretches comprising up to 11 consecutive residues. Such polyacidic regions are found in other proteins (eg. in the RAD6 product of yeast, Reynolds et al., Proc. Natl. Acad. Sci. U.S.A. 82 168–172, 1985), but are of uncertain function. A speculation is that in the KEX1 product, the polyacidic region might be involved in activation of the protein, as it encounters increased acidity in the Golgi compartments (Kelly, Nature 326 14–15, 1987). Such activation could be structural, for example a change to an alpha helical form of the polyacidic domain in acidic conditions, or might involve release of bound metal ions necessary for protease function.

The amino-acid sequence of the KEX1 gene product was compared with known protein sequences using the NBRF protein sequence database. Significant homology was found with the carboxypeptidase Y (CPY)—a well characterized yeast vacuolar serine protease (Hayasi et al. op cit., 1975; Martin et al. op. cit., 1982; Svendsen et al. op. cit., 1982; and see Breddam op. cit., 1985 for a review). The region of homology comprises two tracts, the first of 196 residues situated in the N-terminal part of both proteins. It begins at residue 64 of the KEX1 protein and at residue 22 of mature CPY, or residue 134 of the preproCPY sequence (Valls et al., Cell 48 887–897, 1987). There is then a region of 131 residues in KEX1 with no homology, and a second homology tract commencing at residue 381 of KEX1 and residue 314 of mature CPY which extends for 95 amino acid residues. The overall homology of both tracts (comprising 291 residues) is 39%, but within two sequence blocks the similarity is over 50%. One of these highly conserved regions in the KEX1 protein contains the sequence: GlyGluSerTyrAlaGly 201, which is also within the active site of CPY and includes the active serine residue (Shaw and Wells, Biochem. J. 128 229–235, 1972). To establish whether this serine residue was essential for the activity of the KEX1 gene product we generated a point mutation by oligonucleotide site-directed mutagenesis which changed serine (198) to alanine (198).

Oligonucleotide-directed mutagenesis was carried out as described by Zoller and Smith (1982), using ssDNA of M13mp18 with the 1.1 kb BamHI-SalI fragment of the KEX1 gene and the mutagenic oligonucleotide 5'ATCGGGTGAAGCTTACGCTGGCC 3'. The mutation was detected by the presence of a newly created HindIII site and confirmed by sequencing of the mutated site and the surrounding region. The mutated SalI-BamHI fragment was cloned into SalI-BamHI site of plasmid pAD82, resulting in plasmid pAD26. This plasmid was introduced into a kex1$^-$ mutant and transformants were tested for the killer phenotype. No killer toxin secretion was detected. This result suggests that the KEX1 gene product functionally conserves the active serine of CPY and indicates that the KEX1 protein is a serine protease.

Plasmid pAD81 contains the KEX1 gene on the 3.1 kb HindIII fragment inserted into the pFL44 HindIII site. Plasmid pAD82 is a derivative of pAD81 with the SacI-PstI fragment of the polylinker deleted by SacI/PstI digestion followed by Mung Bean exonuclease and Klenow DNA polymerase I treatment to create blunt ends. Plasmid pFL44 is a 2u DNA based, 4.4 kb, yeast-*E. coli* shuttle vector with URA3 and Ap$^r$ markers and the pUC19 polylinker in lac z' fragment.

EXAMPLE 2: Action of the KEX1 Protease on Killer Toxin Processing

Two regions of the killer protoxin were considered as candidates for KEX1 protease cleavage sites: the P2 site i.e. after the ProArg 44 residues of the leader; and the junction between the $\alpha$ and $\gamma$ polypeptides (See FIG. 1). To check if cleavage at the P2 site depends on the KEX1 gene product, a kex$^-$ mutant (ADY411-9-5) was transformed with a plasmid (pL360-2) in which the 44 amino-acid residues of the preprotoxin leader was replaced by the 17 residue signal sequence of yeast acid phosphatase. This removes the requirement for a P2 cleavage event and allows N-terminal $\alpha$-maturation to proceed with signal peptidase function alone. This plasmid (pL360-2) transformed wild type nonkiller yeast (K−) to the killer phenotype (K+). In cells carrying pL360-2, signal sequence cleavage was sufficient to generate the authentic N-terminus of the $\alpha$ subunit of killer toxin. We reasoned that if the KEX1 protease acted only at the P2 site, yeast harboring this construct would no longer require KEX1 for killer toxin maturation. The kex1$^-$ transformants, however, maintained a (K−) phenotype demonstrating that the KEX1 gene is still required and that the P2 site of the killer protoxin (if it is used at all) is not the only KEX1 cleavage site.

The exact endoproteolytic cleavage site of the protoxin precursor at the junction of the $\alpha$ and $\gamma$ peptides was not known. Based on the migration rate of the $\alpha$ subunit on SDS-polyacrylamide gel electrophoresis, and the inhibition of killer toxin processing by the chymotrypsin inhibitor, TPCK, Trp 130 was proposed as a possible cleavage site (Bostian et al., op. cit. 1984). The AsnArgPro 133 sequence was also a plausible cleavage site, found in some hormone precursors (Schwartz, FEBS Letts. 200, 1–9, 1986). In order to precisely locate the $\alpha/\gamma$ junction, the amino-acid sequence at the C-terminus of the $\alpha$ subunit of the killer toxin has been determined (H. Zhu, H. Bussey, D. Y. Thomas, J. Gagnon, and A. Bell, J. Biol. Chem. in press). The $\alpha$ polypeptide was found to extend 17 amino-acid residues beyond Trp 130 to a C-terminal residue at Ala 147. This residue is followed in the precursor by ArgArg 149, a candidate for a dibasic cleavage site recognized by the KEX2 encoded protease. These findings suggested that the KEX1 protease has a conserved carboxypeptidase function and removes basic residues from the C-terminus of the α subunit following a KEX2 endoprotease cut after ArgArg149. This processing pathway is widespread among eucaryotic precursor proteins, namely an endoprotease cleavage after the dibasic residues followed by a trimming back of the dibasic residues by a carboxypeptidase B-like activity to generate the mature C-terminus of the polypeptide.

EXAMPLE 3: Action of the KEX1 Protease on α-factor Processing

The hypothesis that the KEX1 gene product has a carboxypeptidase B-like activity raises the possibility that it functions in the maturation of the mating pheromone α-factor. The KEX2 endoproteolytic cleavage of the α-factor precursor occurs after LysArg residues and releases a premature form of the pheromone (see FIG. 1). The conversion of this pro-pheromone to the mature α-factor requires subsequent action of dipeptidyl aminopeptidase A and, in the case of the internal pheromone repeats only, a further carboxypeptidase B-like activity to remove the C-terminal dibasic residues. Therefore, if the KEX1 gene product contains a carboxypeptidase B-like activity required for a α-factor maturation, and if the presence of two basic residues at it C-terminus essentially removes the biological activity of the pheromone, then a mutation within the KEX1 locus should lead to reduction in the level of mature α-factor secreted by MAT α yeast. The expected level of the reduction would be about 75%, because the majority of the pheromone secreted from yeast cells in encoded by the MF α 1 gene (Kurjan, Cell 30, 933–943, 1985). This gene has 4 repeated units of the pheromone coding region, with the three internal repeats requiring C-terminal maturation (see FIG. 1).

The α-factor peptide (αF-KR) of sequence $NH_2$-TrpHisTrpLeuGluLeuLysProGlyGluProMetTyr-LysArg-COOH was synthesized on an Applied Biosystem (ABI) Model 430A peptide synthesizer. T-Boc amino acid and standard ABI protocols were used. The peptide was cleaved from its support with HF, desalted and lyophilised. Purification was achieved on a reverse phase semi-preparative column (Vydac TM Protein and Peptide C18, 10×250 mm) with 0.1% TFA/$H_2O$ and a 0.1% TFA/$CH_3CN$ gradient. Amino acid analysis and sequence analysis showed that the purified peptide may have up to 4% of αF-KR with a missing Trp at the N-terminus. This αF-KR peptide had essentially no biological activity on MAT a cells but could be converted to a biologically active form by in vitro treatment with carboxypeptidase B. We then tested pheromone production in vivo, comparing the level of mature α-factor secreted by a wild type strain (Sc25k) and its KEX1 disrupted derivative (Sc25k-13 with the KEX1 gene disrupted by the LEU2 marker). The secretion of active pheromone was monitored by the presence of zones of growth inhibition surrounding cells spotted on a plate seeded with a strain supersensitive to α-factor (sst1 or sst2 mutants—strains XMBL-12b and M171-1c respectively) (Chan and Otte, Mol. Cell Biol., 2, 21–29, 1982). The kex1− mutant generated a zone slightly smaller than the wild strain (S6) and this zone could be restored to wild type size if the kex1− mutant strain carries the plasmid pAD17 containing the KEX1 gene.

In a further test, we examined the effect of the kex1− mutation in a strain where the region coding for the last pheromone repeat in the MF α 1 gene was mutated to render it functionally inactive. To do this, we introduced a deletion into the plasmid pJK6, a YCp50 based plasmid with the MF α 1 coding sequence behind the GAL1 promoter, inserted into the EcoRI-SalI sites of the vector. The deletion resulted in replacement of the 5′C-terminal amino-acid residues of the last α-factor repeat (GlyGlnProMetTyr) by 10 amino-acids of the tetracycline resistance gene from the pBR322 part of the vector (ArgArgGluAlaGlyTrpProSerProLeu). This mutated plasmid, pJK6-4, was constructed as follows. A 1.5 kb SspI-SalI fragment containing the GAL1 promoter and MF α1 coding sequence was isolated from plasmid pJK6, partially digested with NciI, made blunt ended using Klenow DNA polymerase I, digested with EcoRI and ligated into the EcoRI-NruI sites of YCp50. This mutation eliminated the authentic C-terminus of the last pheromone unit and resulted in a peptide that was unlikely to have α-factor activity. The liberation of mature active α pheromone from such a mutated precursor should be strictly dependent on a carboxypeptidase B-like activity. The mutated plasmid (pJK6-4) was introduced into diploid kex1− and KEX1 strains (1315 and Sc25d, respectively). In the diploid cell type the expression of chromosomal copies of the MF α 1 and MF α 2 genes is repressed (Sprague et al. Cell 32, 409–415, 1983). Transcription of the MF α 1 gene in plasmid pJK6-4 occurs under the control of the GAL1 promoter which replaces the intrinsic MF α 1 promotor in this construct. The zone assay revealed that active α-factor was secreted from a galactose-grown wild type diploid, carrying plasmid pJK6-4, but not from the homozygous kex1− mutant. This result is consistent with, and strongly supports, the conclusion that the KEX1 protein is involved in the carboxypeptidase B-like step of α-factor precursor maturation.

If the kex1− null mutant is defective in a carboxypeptidase B-like activity, it will produce and could secrete αF-KR, the inactive pro-pheromone with C-terminal LysArg residues. If this is the case, then the dibasic residues should be removed in vitro by carboxypeptidase B treatment, generating biologically active pheromone, as was found with the synthetic αF-KR. We checked for possible activation by carboxypeptidase B of material secreted by the kex1− mutant. The medium from the culture of the kex1− strain, 1315 carrying plasmid pJK6-4, was passed through a Bio-Rex 70 column and the retained material eluted according to Ciejek et al. Biochem. Biophys. Res. Commun. 78, 952–961, 1977. The eluate was brought to pH 4.0 with ammonium hydroxide, lyophilized and suspended in 100 ul of water. The resultant column eluate had 100 times less pheromone activity than the equivalent eluate from a wild type strain, as determined by a zone test on the α-factor supersensitive mutant, sst2. Both extracts were treated with carboxypeptidase B as described by Wolff et al. (J. Biol. Chem. 237, 3094–3099, 1962) and spotted onto a seeded plate of yeast strain sst2. Significant enhancement in activity was observed for the extract obtained from the kex1− mutant, but no effect was seen in the case of the wild type strain.

We claim:

1. A vector comprising a Saccharomyces DNA KEX1 gene sequence wherein said gene sequence encodes KEX1 product, and a DNA sequence encoding a desired precursor polypeptide, wherein said precursor polypeptide is a substrate for processing by said KEX1 product, said polypeptide is selected from hormones and neuropeptides, and wherein said precursor has basic amino acids at the COOH-terminus and whose KEX-1-dependent removal produces the active protein.

2. The vector of claim 1, wherein said DNA sequence encoding a desired precursor polypeptide is derived from a source foreign to yeast.

3. A host organism transformed by the vector of claim 1.

4. The host organism of claim 3, wherein the host is selected from the group consisting of: *Saccharomyces cerevisiae, Saccharomycopsis lipolytica, Schizosaccharomyces pombe,* filamentous fungi, mammalian cell lines, insect cell lines and other cell types where KEX1 activity is lacking.

5. The vector of claim 1 wherein the basic amino acids are selected from the group consisting of lysine and arginine.

6. A method for the specific processing of precursors of cellular secreted proteins comprising:

(a) providing one of (i) a recombinant vector comprising a DNA KEX1 gene sequence and a second recombinant vector comprising a DNA sequence encoding a precursor of a cellular secreted protein, containing basic amino acid residues at the COOH-terminal and requiring KEX-1-dependent removal of said amino acids for activity, or (ii) a single recombinant vector comprising both said sequences;

(b) transforming a yeast host organism with the recombinant vector or vectors of step (a);

(c) culturing the transformed host cells whereby the DNA of the recombinant vector or vectors express both the encoded KEX1 product and the precursor of the cellular secreted protein;

(d) processing said precursor to said cellular secreted protein whereby the basic amino acid residues at the COOH terminal are removal and whose removal is KEX1-dependent; and (e) recovering said cellular secreted protein from the medium.

7. A method for the specific processing of precursors of cellular secreted proteins comprising:

(a) providing a recombinant vector comprising a DNA sequence encoding the precursor of the cellular secreted protein containing basic amino acid residues at the COOH-terminal and requiring KEX1-dependent removal of said amino acids for activity;

(b) transforming a host yeast strain carrying a null mutation of the KEX1 gene, produced by gene disruption of the KEX1 gene with the recombinant vector of step (a);

(c) culturing the transformed host yeast whereby the DNA of the recombinant vector expresses the precursor cellular secreted protein,; and (d) recovering said precursor of the cellular secreted protein.

8. The method of claim 7 wherein the precursor of the cellular secreted protein is preproinsulin.

* * * * *